| United States Patent [19] | [11] Patent Number: 4,582,528 |
|---|---|
| Gray et al. | [45] Date of Patent: Apr. 15, 1986 |

[54] S-METHYL-N,N-DIETHYL THIOCARBAMATE AS A SELECTIVE HERBICIDE IN RICE

[75] Inventors: Reed A. Gray, Saratoga; Grant K. Joo, Cupertino, both of Calif.

[73] Assignee: Stauffer Chemical Co., Westport, Conn.

[21] Appl. No.: 385,231

[22] Filed: Jun. 4, 1982

[51] Int. Cl.⁴ .................... A01N 37/00; C07C 155/02
[52] U.S. Cl. ....................................... 71/100; 558/232
[58] Field of Search ...................... 260/455 A; 71/100

[56] References Cited
U.S. PATENT DOCUMENTS
3,185,720 5/1965 Tilles et al. ..................... 260/455 A Primary Examiner—Henry R. Jiles
Assistant Examiner—Robert C. Whittenbaugh
Attorney, Agent, or Firm—Michael J. Bradley

[57] ABSTRACT

S-methyl-N,N-diethyl thiocarbamate which has the structural formula

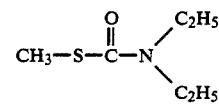

which is useful as a selective herbicide in rice and sorghum.

3 Claims, No Drawings

S-METHYL-N,N-DIETHYL THIOCARBAMATE AS A SELECTIVE HERBICIDE IN RICE

BACKGROUND OF THE INVENTION

An herbicide is a compound which controls or modifies plant growth, e.g. killing, retarding, defoliating, desiccating, regulating, stunting, tillering, stimulating, and dwarfing. "Plants" refer to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control can increase crop yield and reduce harvesting costs.

Herbicidal effectiveness is dependent upon several variables. One of these is the time or growth related method of application. In the past, the most popular methods of application included: pre-plant incorporation into the soil, pre-emergence surface treatment of seeded soil, and post-emergence treatment of the plant and soil.

The most important determinant of herbicidal effectiveness is the susceptibility of the target weed. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre (0.0112 to 56 kilograms per hectare (k/ha)), usually from 0.1 to 25 pounds per acre (0.112 to 28 k/ha). The actual amount used depends upon several considerations, including particular weed susceptibility and overall cost limitations.

Thiocarbamate herbicides are known to be particularly effective in the control of grassy type weeds which interfere with the cultivation of a wide variety of crops, e.g., barley, corn, lentils, peanuts, peas, potatoes, soybeans, spinach, tobacco and tomatoes.

Unfortunately, the thiocarbamates, like many other herbicides, are not selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

The beneficient uses of these herbicides are commonly preserved by the use of antidotal compounds which reduce or eliminate damage to the crop without substantially impairing the ameliorative effect of the herbicide. See U.S. Pat. Nos. 4,021,224 and 4,021,229 and Belgian Pat. No. 846,894.

SUMMARY OF THE INVENTION

The present invention pertains to the discovery that the S-methyl-N,N,-diethylthiocarbamate has the remarkable effect of controlling watergrass and yellow nutsedge weed species when applied at certain rates in a pre-emergence manner, while at the same rate exhibiting no adverse effect to rice and sorghum (milo).

The selectivity toward rice and sorghum that is possessed by the compound of this invention is quite unexpected and surprising in light of the face that homologous compounds are not nearly as effective.

DESCRIPTION OF THE INVENTION

This invention is directed to the use of S-methyl N,N-diethyl thiocarbamate as a selective herbicide for use on rice and sorghum crops. Rice shows a high degree of tolerance to S-methyl-N,N-diethyl thiocarbamate.

The above herbicidal compound can be prepared by the general methods described in *Thiolcarbamates-Preparation and Molar Refractions*, American Chemical Society, 81, 714 (1959). The thiocarbamate compounds are known herbicides and their method of synthesis is well known. See U.S. Pat. Nos. 2,913,327, 2,983,747, 3,133,927, 3,175,897, and 3,185,720, for example. However, in general the thiocarbamates produce unacceptable injury to rice and sorghum crops. Therefore, it is quite unexpected to discover the high degree of tolerance rice and sorghum exhibit toward S-methyl-N,N-diethyl thiocarbamate.

It has been discovered that S-methyl-N,N-diethyl thiocarbamate is particularly effective in control of watergrass and yellow nutsedge. This is particularly unexpected in that extremely close prior art homologs show no such superior control.

The compound of the present invention can be prepared according to the teaching of the following examples.

EXAMPLE I

S-methyl-N,N-diethyl thiocarbamate

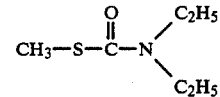

NaSCH$_3$ was prepared by the procedure of Pleininger, Chem. Ber., 83, 265–268 (1950). Under and argon atmosphere 220 cubic centimeters (cc) anhydrous methanol was reacted with 10 grams (g) (0.43 mole) sodium to form NaOCH$_3$. Methanethiol (25 g, 0.52 mole) cooled to 0° C. was added rapidly to the NaOCH$_3$, stirred for a few minutes and 130 cc of methanol was distilled at reflux. Toluene (350 cc) was slowly added to the refluxing solution and distilled. An additional 300 milliliters (ml) of toluene was added and distilled until 500 cc of a toluene-methanol distillate was collected. Diethyl carbamyl chloride (58.4 g, 54.5 cc, 0.43 mole) was added over 11 minutes. The reaction mixture was then refluxed for 2 hours, cooled, filtered, washed with two 50 cc portions of toluene and the filtrate evaporated on a steam bath. The product, 33 g of a liquid, was fractionated. The fraction from 132.5° C. to 133.0° C. was recovered as product, 22.38 g of a liquid having an $n_D^{27}$ of 1.4854. Yield was 35.4% of theoretical of the title compound. This compound will be referred to as Compound No. 1.

Compound No. 1 was comparatively tested with other thiocarbamate herbicides for selectively controlling watergrass [*Echinochloa crusgalli* (L.) Beauv.] and yellow nutsedge [*Cyperus esculentus* (L.) by pre-emergent application on these weeds and rice. ]

The additional herbicides tested included S-ethyl N,N-dipropyl thiocarbamate, described in U.S. Pat. No. 2,913,327 and commercially available as EPTAM ®, (Compound No. 2); S-ethyl N-ethyl N-cyclohexyl thoicarbamate, described in U.S. Pat. No. 3,185,720 and commercially available as RO-NEET ®, (Compound No. 4); and S-propyl N,N-dipropyl thiocarbamate, described in U.S. Pat. No. 2,913,327 and commercially available as VERNAM®, (Compound No. 3).

Pre-Emergence Herbicide Screening Test

Eleven aluminum flats measuring 8.5×6.0×2.75 inches were filled with San Jose sandy loam soil. The soil had a pH of 7.3, and contains 2% organic matter, 41.6% sand, 46.4% silt and 12% clay. One flat of soil was treated with Compound No. 1 at 3 lb/A by incorporating an acetone solution of the compound into the soil using a small 5-gallon cement mixer. Another flat received Compound No. 1 at 6 lb/A. Other flats were treated the same way with Compound Nos. 2, 3, and 4 at 3 and 6 lb/A, and one flat was left untreated as a control. One row of watergrass, two rows of yellow nutsedge tubers, one row of Amak R-10 milo (sorghum), one row of Calrose rice and one row of M-9 rice seeds were planted 0.5 inch deep in each flat of soil. The flats were watered lightly by sprinkling and placed in the greenhouse at 70–90° F. The results taken after 20 days are shown in Table I.

The percent control is based on the total injury to the plants due to all factors of injury. The rating system is from 0 to 100 percent, where the value represents percent control. For example, 0 represents no herbicidal effect with growth equal to untreated controls and 100 represents complete control. The results are reported in Table I.

TABLE I

| Compound Number | Application Rate | % Control or Injury 20 Days After Treatment | | | | |
|---|---|---|---|---|---|---|
| | | Watergrass | Yellow Nutsedge | Calrose Rice | M-9 Rice | Milo |
| Control | | 0 | 0 | 0 | 0 | 0 |
| 1 | 3 lb/A | 70 | 90 | 0 | 0 | 0 |
| | 6 lb/A | 80 | 99 | 0 | 0 | 25 |
| 2 | 3 lb/A | 90 | 99 | 100 | 100 | 99 |
| | 6 lb/A | 99 | 100 | 100 | 100 | 100 |
| 3 | 3 lb/A | 96 | 100 | 90 | 95 | 100 |
| | 6 lb/A | 98 | 100 | 99 | 99 | 100 |
| 4 | 3 lb/A | 75 | 96 | 100 | 100 | 35 |
| | 6 lb/A | 90 | 100 | 100 | 100 | 65 |

The compound of the present invention is useful as an herbicide, especially as a pre-emergence herbicide, and can be applied in a variety of ways at various concentrations. The compound is applied to the soil where control of undesirable vegetation is desired. Preferably, the pre-emergence application is made a day or two before planting of the rice of milo crop, on the date of planting or a day or two after planting of the rice or milo.

In the preferred practice, the compound herein defined is formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the material in a given application. Thus, the active herbicidal compound may be formulated as granules of relatively large particle size, as wettable powders, as emulsifiable concentrates, as powdery dusts, as solutions or as any of several other known types of formulations, depending upon the desired mode of application.

Preferred formulations for pre-emergence herbicidal applications are wettable powders, emulsifiable concentrates and granules. These formulations may contain as little as about 0.5% to as much as about 95% or more by weight of active ingredient.

Crop injury and herbicidal effectiveness depends upon several factors, including the nature of the soil where control is desired and the types of seeds or plants to be controlled. Therefore, the rate of application can vary from about 0.1 to about 10 pounds per acre, preferably from about 0.1 to about 5 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, koalin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogenous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general compromises about 0.5% to 95% of active ingredient by weight of the herbicidal composition.

Granular formulations wherein the toxicant is carried on relatively coarse particles, are usually applied without dilution to the area in which suppresion of vegetation is desired. Typical carriers for granular formulations include sand, fuller's earth, bentonite clays, vermiculite, perlite and other organic materials which absorb or which may be coated with the toxicant. Granular formulations normally are prepared to contain about 5% to about 25% of active ingredients which may include surface-active agents such as heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their sodium salts; polyhdric alcohols; and other types of surface-active agents, many of which are available in commerce. The surface-active agent, when used, normally comprises from 0.1% to 15% by weight of the herbicidal composition.

Dusts, which are free-flowing admixtures of the active ingredients with finely divided solids such as talc, clays, flours and other organic and inorganic solids which act as dispersents and carriers for the toxicant, are useful formulations for soil-incorporating application. Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected. Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide can also be applied in the crop furrow or it can be applied by injection along-side the crop and furrow in rows spaced several inches from the seed.

What is claimed is:

1. A method of selectively controlling undesirable vegetation in rice and sorghum comprising applying an herbicidally effective amount of S-methyl N,N-diethyl thiocarbamate.

2. S-methyl N,N-diethyl thiocarbamate.

3. A herbicidal composition comprising a herbicidally effective amount of S-methyl-N,N-diethyl thiocarbamate and an inert carrier.

* * * * *